US010660376B2

(12) United States Patent
Thompson

(10) Patent No.: US 10,660,376 B2
(45) Date of Patent: May 26, 2020

(54) RADIATION BRA EXTENDER

(71) Applicant: Elizabeth Chabner Thompson, Scarsdale, NY (US)

(72) Inventor: Elizabeth Chabner Thompson, Scarsdale, NY (US)

(*) Notice: Subject to any disclaimer, the term of this patent is extended or adjusted under 35 U.S.C. 154(b) by 0 days.

(21) Appl. No.: 16/116,218

(22) Filed: Aug. 29, 2018

(65) Prior Publication Data
US 2019/0059458 A1 Feb. 28, 2019

Related U.S. Application Data

(60) Provisional application No. 62/552,103, filed on Aug. 30, 2017.

(51) Int. Cl.
| *A41C 3/00* | (2006.01) |
| *A41F 1/00* | (2006.01) |
| *A61B 18/18* | (2006.01) |
| *A61N 5/10* | (2006.01) |
| *A41F 15/00* | (2006.01) |

(52) U.S. Cl.
CPC .......... *A41C 3/0064* (2013.01); *A41C 3/0028* (2013.01); *A41F 1/006* (2013.01); *A41F 15/002* (2013.01); *A61B 18/18* (2013.01); *A61N 5/1049* (2013.01); *A61N 2005/1097* (2013.01)

(58) Field of Classification Search
CPC ......... A41C 3/00; A41C 3/028; A41C 3/0064; A41C 3/0071; A41C 3/02; A41C 3/0028
USPC .................................. 450/81, 86, 58, 79
See application file for complete search history.

(56) References Cited

U.S. PATENT DOCUMENTS

| 3,311,112 | A | * | 3/1967 | Murray | ................... A41F 1/006 450/1 |
| 3,826,266 | A | * | 7/1974 | Alpert | ................... A41C 3/0071 450/11 |
| 5,496,605 | A | * | 3/1996 | Augst | ................. A61F 13/0273 428/43 |
| 5,616,387 | A | * | 4/1997 | Augst | ................. A61F 13/0273 428/43 |
| 6,200,194 | B1 | | 3/2001 | Grier | |
| 6,336,839 | B1 | * | 1/2002 | Valli | ......................... A41C 3/00 450/1 |
| 6,994,606 | B2 | * | 2/2006 | Li | ............................. A41C 3/02 24/197 |
| 7,001,240 | B1 | * | 2/2006 | Huffman-Jimenez | ...................... A41C 3/0028 450/58 |
| 8,753,171 | B2 | * | 6/2014 | Thompson | ........... A41C 3/0064 450/79 |
| 9,277,963 | B2 | * | 3/2016 | Thompson | ........... A41C 3/0064 |
| 2007/0123148 | A1 | | 5/2007 | Heer | |
| 2012/0220193 | A1 | | 8/2012 | Thompson | |
| 2015/0073254 | A1 | | 3/2015 | Talant | |

OTHER PUBLICATIONS

International Search Report and Written Opinion issued in International PCT Application No. PCT/US2018/048930 and dated Nov. 30, 2018.

* cited by examiner

*Primary Examiner* — Gloria M Hale
(74) *Attorney, Agent, or Firm* — Kaplan Breyer Schwarz, LLP

(57) ABSTRACT

An extender for a radiation treatment bra extends the "circumference" of the RTB, enabling it to accommodate a relatively larger back size for a given sized RTB.

20 Claims, 5 Drawing Sheets

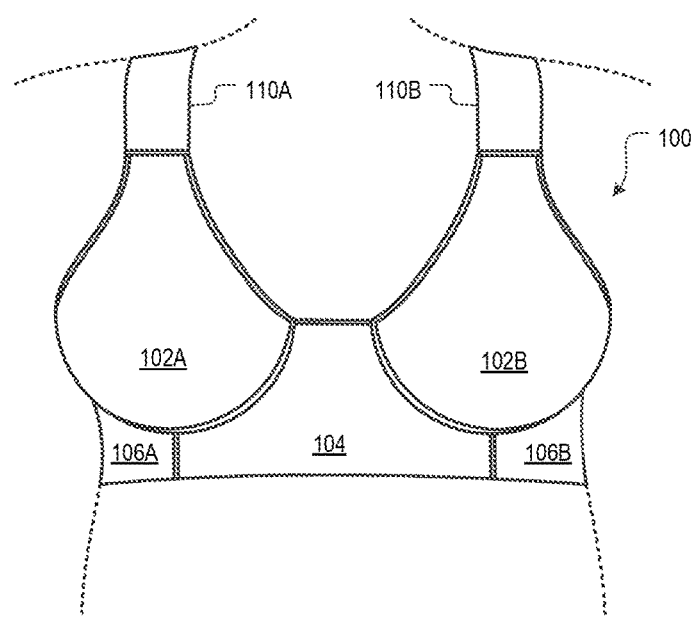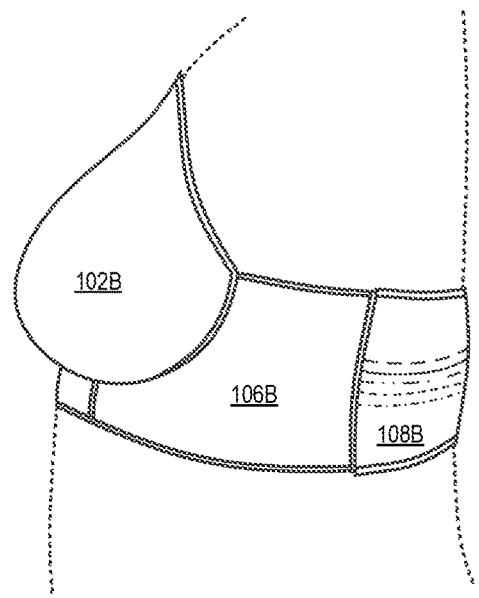
FIG. 1A
Prior Art
FIG. 1B
Prior Art

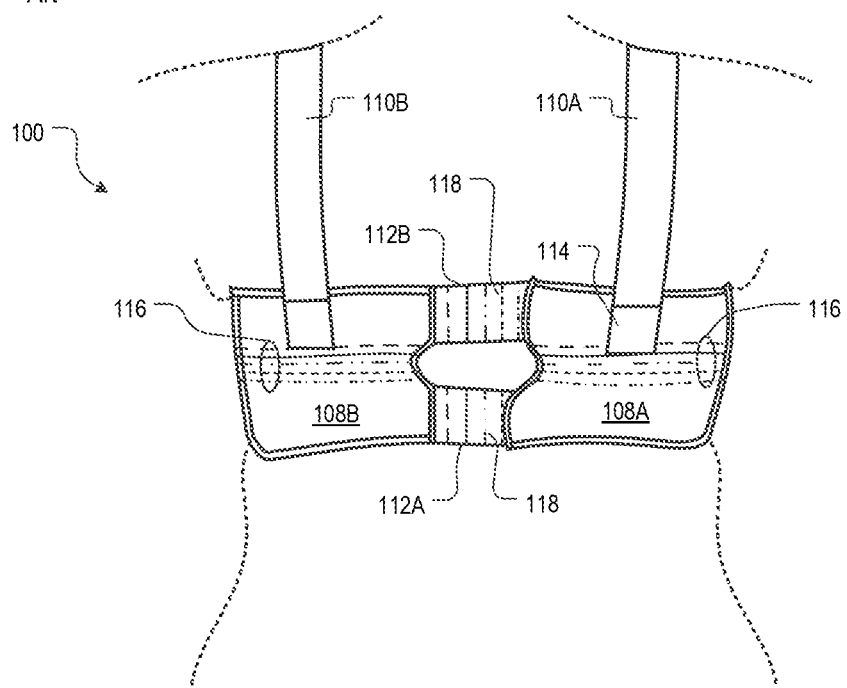

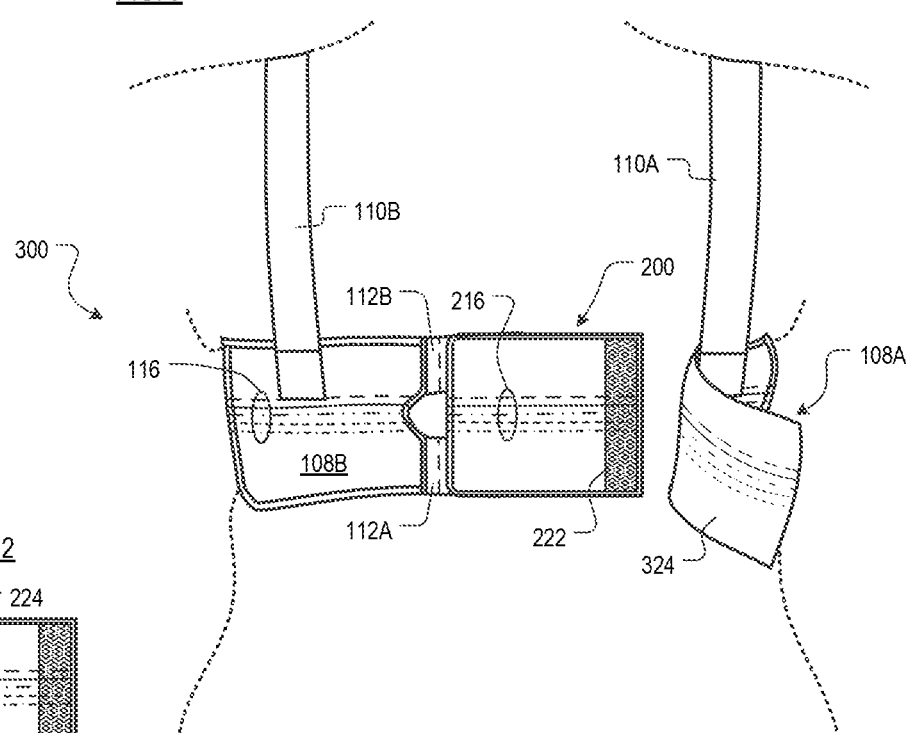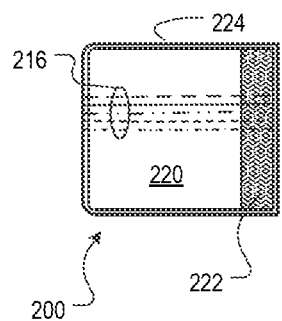

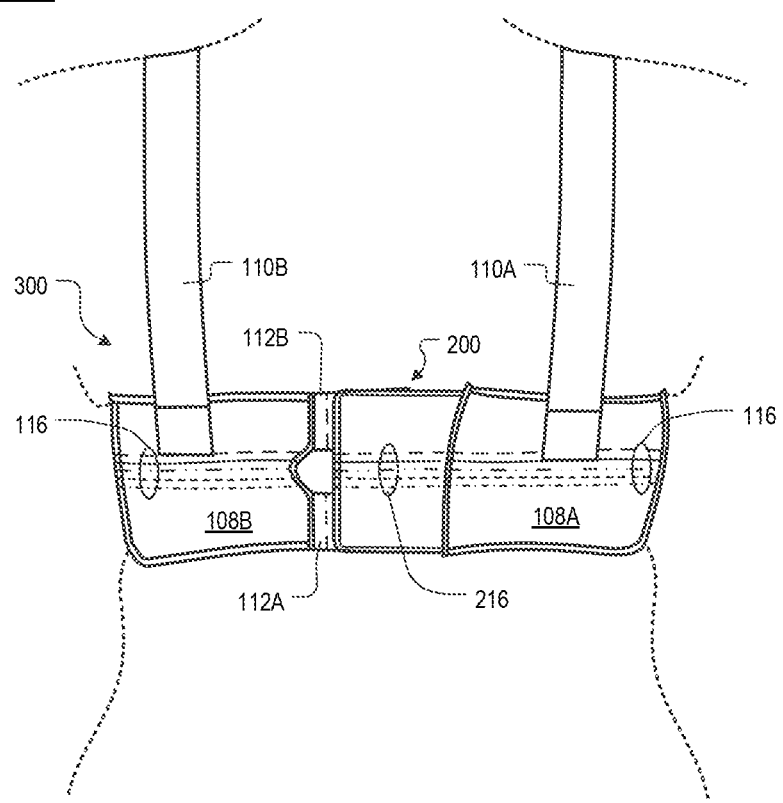

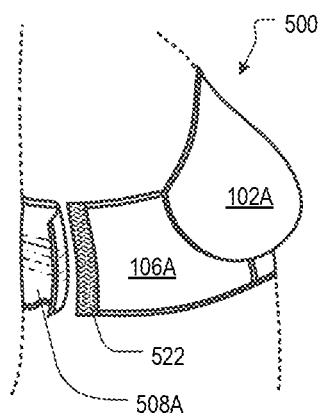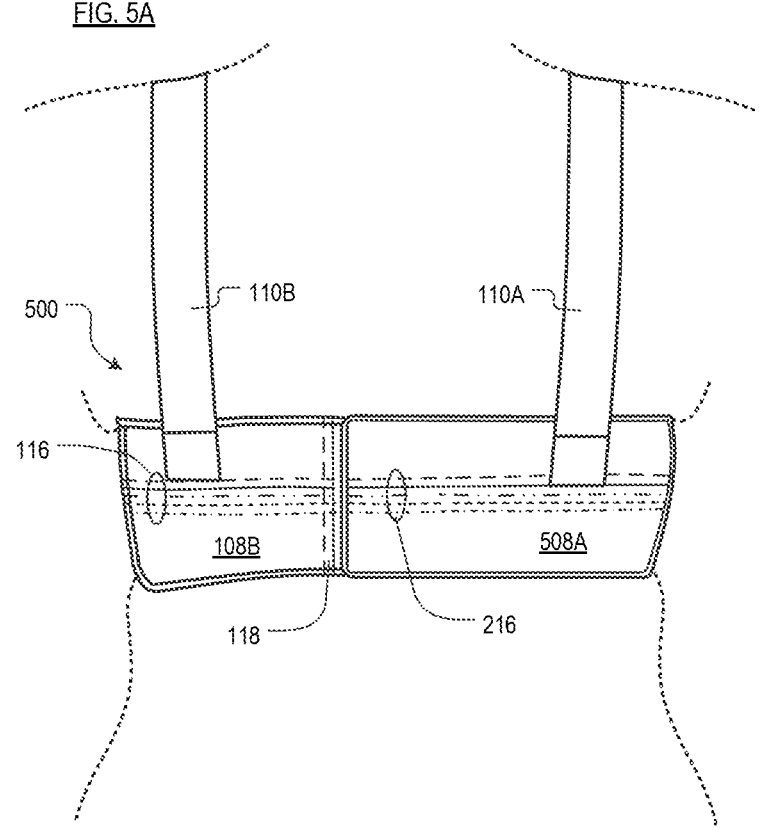

RADIATION BRA EXTENDER

STATEMENT OF RELATED CASES

This disclosure claims priority to U.S. Pat. Application 62/552,103, which was filed Aug. 30, 2017 and is incorporated herein by reference. This disclosure also pertains to U.S. Pat. Nos. 8,753,171 and 9,277,963, both of which are incorporated herein by reference.

FIELD OF THE INVENTION

The present invention relates to radiation oncology in general and, more particularly, to garments for a patient undergoing a radiation treatment.

BACKGROUND OF THE INVENTION

Applicant's U.S. Pat. Nos. 8,753,171 and 9,277,963 disclose a radiation treatment brassiere ("RTB") that is worn during a radiation treatment session. The RTB is capable of precisely and reproducibly obtaining a desired breast geometry, treatment position, and patient-to-machine alignment for radiation therapy while also enabling the non-affected breast to be moved out of the treatment field.

The RTB includes sheer, substantially "see-through" cup material, and multiple adjustment elements/closures. The bra is devoid of metal and uses hook-and-loop fastener (e.g., VELCRO®, etc.). The RTB can be worn for use with all treatment machines without causing bolus effect and is undetectable during CT scan.

Multiple adjustable elements, typically implemented as closures, enable the position of the breast to be adjusted to achieve a desired reference breast geometry during a radiation treatment planning session. This is achieved by appropriately tightening or loosening the various adjustable elements, thereby establishing a "reference setting" for each such adjustable element. The RTB includes markings (e.g., lines, etc.) to facilitate memorializing the reference setting. This enables a technician to reset all released closures to their established reference settings prior to a radiation treatment session. Since the reference setting for each adjustable element establishes the reference breast geometry, the reference breast geometry is re-established for each radiation treatment session by simply resetting each released adjustable closure to its reference setting.

The RTB also provides an ability to move the non-treated breast laterally to avoid, to extent possible, placing medial tissue of the contralateral breast in the treatment field.

Although the RTB, by virtue of its construction, is adjustable, it must nevertheless properly fit the patient to be able to establish a precise, reproducible breast geometry, as is required for proper breast-to-treatment machine alignment. For this reason, the RTB, which is now commercially available from CIVCO Radiotherapy of Coralville, Iowa as the Chabner XRT® Radiation Bra, is available in a number of sizes, covering a range of back sizes and cup sizes.

Notwithstanding the variety of size options available, it is still possible that a patient will not fit properly into an RTB. Consider, for example, a size "3" RTB, which accommodates a back size of 38" to 40" and a cup size of B/C, and a size "4" RTB, which accommodates a back size of 38" to 40" and a cup size of D/DD. A patient might fit a size "3" RTB by breast/cup size, but has a large back that is not properly accommodated by a size "3" RTB. In such a scenario, sizing up to a size "4" would not be a good option. Or, consider another scenario in which a patient is too large to fit into the largest size RTB that is offered.

SUMMARY

The present invention addresses the aforementioned issue by providing a RTB extender, which extends the "circumference" of the RTB, enabling it to accommodate a relatively larger-than-nominal back size for any particular RTB.

In the illustrative embodiment, the RTB extender has a quadrilateral shape, typically square or rectangular, and has a size that is suitable for coupling to the RTB. For example, the "height" (distance between the upper and lower edges) of the RTB extender is substantially the same as the "height" of the back panels of the RTB. In some embodiments, the RTB extender comprises the same material as the back panels of the RTB.

In the illustrative embodiment, the RTB extender is inserted at the back closing of the RTB, between opposing back panels. In embodiments in which the RTB uses hook-and-loop fastener (Velcro®) as closures (e.g., a strip of "hooks," etc.), the RTB extender comprises material appropriate for coupling thereto (e.g., a fabric blend that is hook-and-loop compatible).

To facilitate alignment and establishing reference settings, the RTB extender includes indexing features, such as lines, that are consistent in form and identification, as appropriate, with indexing features found on the RTB.

In some embodiments, the invention provides an extender for a RTB. The extender has a first surface comprising:
  A. At least one of (1) hook-and-loop compatible material or (2) a strip of hook portions of hook-and-loop fastener; and
  B. An indexing feature, wherein the indexing feature is compatible for use with an indexing feature found on portions of a standard RTB.

The extender further comprises a second surface comprising:
  A. At least one of (1) hook-and-loop compatible material or (2) a strip of hook portions of hook-and-loop fastener.

The extender consists of material that will not scatter or attenuate treatment radiation.

In some other embodiments, the invention provides a kit that includes an RTB and an extender. The extender increases a circumference of the RTB when the extender is coupled thereto, and the extender is dimensioned and arranged to couple to the RTB between a first back panel and a second back panel thereof. In some alternative embodiments of the kit, the extender replaces one of the back panels of the RTB. The first and second back panels have an indexing feature for memorializing a position of shoulder straps of the RTB. In some embodiments, the RTB extender has an indexing feature that is compatible with the indexing feature used on the first and second back panels.

In yet some further embodiments, the invention provides an improved RTB, wherein rather than having two "standard-size" back panels, the RTB includes one "standard-size" back panel and a second panel that is selected at the time of fitting so that the RTB will have a circumference that is custom sized for a patient's back width. The improved RTB includes:
  a first cup and a second cup;
  a first shoulder strap coupled, at a first end thereof, to the first cup;
  a second shoulder strap coupled, at a first end thereof, to the second cup;

a first side panel coupled to the first cup and a second side panel coupled to the second cup;

a first back panel coupleable to the first side panel and that couples to a second end of the first shoulder strap, the first back panel having a first indexing feature for memorializing a position of the first shoulder strap;

a second back panel coupleable to the second side panel and that couples to a second end of the second shoulder strap, the second back panel having the first indexing feature for memorializing a position of the second shoulder strap;

wherein, for a RTB having a first size, the first back panel will have a standard length that is the same for all RTBs having the first size, and the second back panel will have a length that is not the same for all RTBs having the first size, but, rather, the length of the second back panel is dependent on a width of a wearer's back.

BRIEF DESCRIPTION OF THE DRAWINGS

FIG. 1A depicts a front view of prior-art RTB 100.
FIG. 1B depicts a side view of prior-art RTB 100.
FIG. 1C depicts a back view of prior-art RTB 100.
FIG. 2 depicts RTB extender 200 in accordance with the illustrative embodiment of the present invention.
FIG. 3 depicts a back view of RTB 300 in accordance with the illustrative embodiment, wherein RTB extender 200 is inserted between the back panels of RTB 100.
FIG. 4 depicts a back view of RTB 300 wherein both back panels coupled to RTB extender 200 of FIG. 2.
FIG. 5A depicts a back view of RTB 500 having one standard-size back panel and one back panel that is selected at the time of fitting, in accordance with an embodiment of the invention.
FIG. 5B depicts a side view of RTB 500, showing where custom-selected-length back-pack panel 508A couples to side panel 106A.

DETAILED DESCRIPTION

The following terms are defined for use in this disclosure and in the appended claims:

"Radiation Treatment Bra" or "RTB" means a brassiere used during radiation treatment, such as for breast cancer. The RTBs to which this definition applies consist of materials that will not substantially attenuate or scatter treatment radiation. So, to the meet this definition, the brassiere cannot include, among other materials, metal or hard plastic. Furthermore, to meet the definition, the cups, side panels, and shoulder straps, and back panels of the RTB comprise a flexible, pliable material; these elements cannot be rigid or inflexible. As a minimum, the cups, side panels, and shoulder straps are made of a sheer material, and the shoulder straps and side and center panels comprise thermoplastic polyurethane (TPU). The RTB includes indexing features, such as lines, to memorialize the position of the shoulder straps on the back panels and the position of the back panels with respect to one another. Examples of brassieres meeting the definition of RTB include the brassieres disclosed in U.S. Pat. Nos. 8,753,171 and 9,277,963. Additionally, the Chabner XRT® brand radiation bra, available from CIVCO Radiotherapy, satisfies the definition.

"Standard-Size" means, when used in the context of an RTB, stock sizes of the RTB or sizes of elements included within a stock-size RTB, as available from a manufacturer. For example, a size "3" RTB, which fits a back size of 38" to 40" and a cup size of B/C, is a standard-size RTB and includes standard-size back panels.

"Hook-and-Loop Compatible Material" means fabric that is able to attach to the rough, "hook" portion of hook-and-loop fastener.

"Substantially" means, when used synonymously with the term "about," +/−15% of a stated value.

"Height" means, in the context of a dimension of the back panels of an RTB and an extender for an RTB in accordance with the present teachings, the distance between a lower edge and upper edge thereof, wherein "lower" and "upper" refer to the positions of edges when the RTB is worn.

FIGS. 1A, 1B, and 1C depict respective front, side, and back views of prior-art RTB 100, as worn by a patient. RTB 100 includes cups 102A and 102B, front panel 104, side panels 106A and 106B, back panels 108A and 108B, and shoulder straps 110A and 110B.

Front panel 104 is sewn to the lower medial portion of cups 102A and 102B, and also to each of side panels 106A and 106B below the cups. Shoulder strap 110A is sewn to the upper edge of cup 102A and shoulder strap 110B is sewn to the upper edge of cup 102B. Back panel 108A is either removably or permanently attached to side panel 106A and back panel 108B is either removably or permanently attached to side panel 106B. In the case in which one or both of the back panels are removably attached to the side panels, hook-and-loop fastener (i.e., VELCRO®) may be used for that purpose. In the case in which one or both of the back panels are permanently attached to the side panels, they are typically sewn thereto.

Shoulder straps 110A and 110B removably couple to respective back panels 108A and 108B. Hook-and-loop fastener 114, a portion of which is disposed on the body-facing side of the shoulder straps, is used for this purpose. Back panels 110A and 110B include indexing feature 116. The indexing feature is used to memorialize the position of the shoulder straps; that is, how far down they extend onto the back panels. Notice that the shoulder straps need not extend downward by the same amount. In the illustrative embodiment, the indexing feature is a group of horizontal lines. In the commercial version of RTB 100, the lines are formed from thread, each line having a different color, such as, for example: purple, green, blue, red, and black (top to bottom).

In the illustrative embodiment, back closures 112A and 112B extend from one or the other of the back panels (i.e., from back panel 110B in the illustrative embodiment). The outward-facing surface of closures 112A and 112B comprise a portion of hook-and-loop fastener (not depicted for clarity) by which they removably couple to the body-facing surface of the opposed back panel (back panel 110A in the illustrative embodiment). The outward-facing surface of back closures 112A and 112B include indexing feature 118, in this case to memorialize the position of the back panels with respect to one another. In the illustrative embodiment, indexing feature 118 is a group of vertical lines 118. In the commercial version of RTB 100, the lines appear in different color: purple, green, blue, red, and black (left to right in the figure).

In some other embodiments, back panels 108A and 108B serve as the closures. That is, hook-and-loop fastener material is incorporated on one or both of the back panels. In some embodiments, the "hook" material of the hook-and-loop fastener is incorporated onto either the outward-facing surface or the body-facing surface of one of the panels, whereas the other panel comprises hook-and-loop compatible material. In such an embodiment, the back closure that is intended to be "overlapped" as the RTB is closed includes indexing feature 118, such as the vertical lines that appear on closures 112A and 112B in the illustrative embodiment. As in the case of the closures, indexing feature 118 memorializes the position of the back panels with respect to one another.

Seams are located on the outside of RTB 108 for patient comfort. Cups 102A and 102B, front panel 104, side panels 106A and 106B, and shoulder straps 110A and 110B are formed of a sheer material that will not block, scatter, or otherwise attenuate treatment radiation. Back panels 108A and 108B, while not necessarily formed of a sheer material, will not block, scatter, or otherwise substantially attenuate radiation. In some embodiments, the "hook-and-loop compatible material;" that is, the "loops," comprises a mix of nylon and spandex. This material is used, for example and without limitation, for back panels 108A and 108B. In some embodiments, cups 102A and 102B are formed from a knit comprising nylon and spandex. In some embodiments, front panel 104, side panels 106A and 106B, and shoulder straps 110A and 110B comprise thermoplastic polyurethane (TPU). Additionally, in some embodiments, the thread used throughout the RTB is polyester, and "hook" material is polyester.

FIG. 2 depicts the outward-facing surface of RTB extender 200 in accordance with the present teachings. The RTB extender has a quadrilateral shape and is dimensioned for consistency with back panels 108A and 108B. The outward-facing surface of RTB extender 200 comprises panel 220 and strip 222 of the "hook" portion of hook-and-loop fastener. The balance of RTB extender 200 comprises the same material as back panels 108A and 108B. In the illustrative embodiment, the RTB extender 200 and back panels 108A and 108B comprises a hook-and-look fastener compatible material. That is, they are capable of coupling to the "hook" material of hook-and-loop fastener. In the illustrative embodiment, RTB extender 200 further includes indexing feature 216, which is the same as, or otherwise compatible for use with, indexing feature 116 on back panels 108A and 108B. In the illustrative embodiment, indexing feature 216 is a group of horizontal lines, consistent in spacing, orientation, and identifying feature(s) (e.g., color, numerical indications, etc.) with the lines on the back panels.

FIG. 3 depicts RTB 300, wherein RTB extender 200 is coupled to RTB 100. With the exception of RTB extender 200, RTB 300 is otherwise identical to RTB 100. That is, RTB 300 includes cups 102A and 102B, front panel 104, side panels 106A and 106B, back panels 108A and 108B, and shoulder straps 110A and 110B.

As depicted in FIG. 3, body-facing surface 224 of RTB extender 200 couples to back closures 112A and 112B. More particularly, the "hook" portions of the hook-and-loop fastener on the outward-facing surface of closures 112A and 112B couple to body-facing surface 224 of RTB extender 200, which comprises hook-and-loop compatible material. In FIG. 3, back panel 108A is not coupled to RTB extender 200. To effect such coupling, body-facing surface 324 of back panel 108A is brought into contact with strip 222 of the "hook" portion of the hook-and-loop fastener on RTB extender 200.

FIG. 4 depicts RTB 300 via a back view. In FIG. 4, both back panels are coupled to RTB extender 200.

Depending upon the size of a patient's back, shoulder strap 110A might couple to back panel 110A, or, alternatively, the shoulder strap might more appropriately couple to RTB extender 200.

In the illustrative embodiments, back panels 108A and 108B couple to respective side panels 106A and 106B via hook-and-loop fastener. As long as the back panels removably couple to the side panels (rather than being permanently attached thereto), some additional embodiments are possible. For example, in an alternative embodiment of RTB 300, one of the (standard-size) back panels, such as back panel 108A, is removed and replaced by a longer or shorter RTB extender 200 in situations in which a standard size is not suitable. That is, when RTB extender 200 is coupled to the RTB, one of the existing standard-size back panels is replaced by the extender.

FIGS. 5A and 5B depicts RTB 500, which is a further embodiment of the invention. RTB 500 is designed such that there is no standard back size for the RTBs; only standard cup sizes. In other words, the RTB is designed to be fully customizable for a patient's back size by selecting, at the time of fitting, back panel 508A having an appropriate length (wherein the "length" of a back panel (or an extender) is the distance between the left and right edges thereof). In the embodiment depicted in FIGS. 5A and 5B, the RTB has an alternative configuration previously discussed; that is, the back panels serve as the closures.

In the embodiment depicted in FIGS. 5A and 5B, the outward-facing surface of side panel 106A includes strip 522 of "hooks" of hook-and-loop fastener. The body-facing surface of back panel 508A comprises hook-and-loop compatible material, such that the back panel and side panel are capable of releasably coupling to one another. Although not depicted in FIG. 5A, the outward-facing surface of "standard-size" back panel 108B includes a strip of hooks of hook-and-loop fastener for releasably coupling to the hook-and-loop compatible material on the body facing surface of back panel 508A.

It will be understood that the hook-and-loop fastening material, or hook-and-loop compatible fastening material, can be located on either of two surfaces that are being coupled to one another. That is, the "hooks" may be located on either of two surfaces being mated, and, likewise, hook-and-loop compatible material will be located on the other of the surfaces.

It is to be understood that many variations of the invention can easily be devised by those skilled in the art after reading this disclosure and that the scope of the present invention is to be determined by the following claims.

What is claimed is:

1. An article comprising an extender for a radiation treatment brassiere, wherein the extender increases a circumference of the radiation treatment brassiere when the extender is coupled thereto, the extender having:
   a first surface, the first surface comprising at least one of hook-and-loop compatible material and a strip of hook portions of hook-and-loop fastener, the first surface further comprising an indexing feature, wherein the indexing feature is compatible for use with an indexing feature found on portions of the radiation treatment brassiere;
   a second surface, the second surface comprising at least one of hook-and-look compatible material and a strip of hook portions of hook-and-loop fastener; and
   wherein neither the first surface nor the second surface of the extender scatters or attenuates treatment radiation.

2. The article of claim 1 wherein the extender has a quadrilateral shape.

3. The article of claim 1 wherein the indexing features comprises a group of lines.

4. The article of claim 3 wherein each line in the group thereof is formed from thread.

5. The article of claim 3 wherein each line is a different color from other lines in the group.

6. The article of claim 5 wherein the colors of the lines include purple, green, blue, red, and black.

7. The article of claim 1 wherein when the extender is in use, it couples to at least one back panel of the radiation treatment brassiere.

8. The article of claim 1 wherein when the extender is in use, it couples to two back panel of the radiation treatment brassiere.

9. The article of claim 8 wherein the extender has a height that is substantially the same as a height of the back panels.

10. The article of claim 1 further comprising the radiation treatment brassiere, wherein the extender and the radiation treatment brassiere therefore compose a kit.

11. An extender for a radiation treatment brassiere, wherein the extender increases a circumference of the radiation treatment brassiere when the extender is coupled thereto, and wherein the extender is dimensioned and arranged to couple to a first back panel of the radiation treatment brassiere having an indexing feature, and further wherein the extender has an indexing feature that is compatible for use with the indexing feature on the first back panel of the radiation treatment brassiere.

12. The extender of claim 11 and further wherein the extender is dimensioned and arranged to couple to a second back panel of the radiation treatment brassiere having an indexing feature, and further wherein the indexing features on the first back panel and the second back panel are the same.

13. The extender of claim 11 wherein radiation treatment brassiere has the first back panel and a second back panel, and further wherein, prior to use, the second back panel is removed and replaced with the extender.

14. The extender of claim 11 wherein the indexing feature comprises a group of lines, wherein the lines are parallel to one another and, when the extender and radiation treatment brassiere are worn by a patient, the lines are substantially horizontal.

15. A radiation treatment brassiere comprising:
a first cup and a second cup;
a first shoulder strap coupled, at a first end thereof, to the first cup and a second shoulder strap coupled, at a first end thereof, to the second cup;
a first side panel coupled to the first cup and a second side panel coupled to the second cup;
a first back panel couplable to first side panel and that couples to a second end of the first shoulder strap, the first back panel having a first indexing feature for positioning the first shoulder strap; and
a second back panel couplable to the second side panel and that couples to a second end of the second shoulder strap, the second back panel having the first indexing feature for positioning the second shoulder strap;
wherein, for a radiation treatment brassiere having a first size suitable for accommodating a first range of wearer back circumferences, the first back panel has a first length that is the same for all radiation treatment brassieres having the first size, and the second back panel has a second length that is not the same for all radiation treatment brassieres having the first size, the second length thus being variable to provide a circumference for the radiation treatment brassiere that it outside the first range of circumferences, thereby providing a relatively better fit for a wearer of the radiation treatment brassiere.

16. The radiation treatment brassiere of claim 15 wherein at least one of the first back panel and the second back panel has a second indexing feature, wherein the second indexing feature is used for positioning the first back panel and the second back panel relative to one another.

17. The radiation treatment brassiere of claim 15 wherein the first indexing feature comprises a plurality of lines that, when the radiation treatment brassiere is worn, are oriented horizontally.

18. The radiation treatment brassiere of claim 16 wherein the second indexing feature comprises a plurality of lines that, when the radiation treatment brassiere is worn, are oriented vertically.

19. A kit comprising a radiation treatment bra radiation treatment brassiere and an extender, wherein the extender increases a circumference of the radiation treatment brassiere when the extender is coupled thereto, and wherein the extender is dimensioned and arranged to couple to the radiation treatment brassiere between a first back panel and a second back panel thereof, and wherein the first and second back panels have an indexing feature for positioning shoulder straps of the radiation treatment brassiere.

20. The kit of claim 19 and further wherein the extender has an indexing feature that is compatible for use with the indexing feature on the first back panel and the second back panel of the radiation treatment brassiere.

\* \* \* \* \*